US006988410B2

(12) United States Patent
Gilmore et al.

(10) Patent No.: US 6,988,410 B2
(45) Date of Patent: Jan. 24, 2006

(54) INSPECTION METHOD AND APPARATUS FOR DETERMINING INCIPIENT MECHANICAL FAILURE

(75) Inventors: Robert Snee Gilmore, Charlton, NY (US); Michael Francis Gigliotti, Jr., Scotia, NY (US)

(73) Assignee: General Electric Company, Niskayuna, NY (US)

( * ) Notice: Subject to any disclaimer, the term of this patent is extended or adjusted under 35 U.S.C. 154(b) by 17 days.

(21) Appl. No.: 10/692,608

(22) Filed: Oct. 24, 2003

(65) Prior Publication Data

US 2005/0087016 A1    Apr. 28, 2005

(51) Int. Cl.
*G01N 29/04* (2006.01)
*A61B 8/00* (2006.01)

(52) U.S. Cl. .......................... 73/600; 73/602; 73/631; 600/458

(58) Field of Classification Search .................. 73/574, 73/577, 579, 589, 596, 599, 600, 627, 628, 73/629, 631, 602; 600/441, 443, 447, 458
See application file for complete search history.

(56) References Cited

U.S. PATENT DOCUMENTS

| 4,265,120 | A | * | 5/1981 | Morris et al. .................. 73/600 |
| 6,132,377 | A | * | 10/2000 | Bolorforosh et al. ........ 600/458 |
| 6,197,130 | B1 | | 3/2001 | Cantrell et al. ............. 148/508 |
| 6,226,228 | B1 | | 5/2001 | Hossack et al. ............ 367/138 |
| 6,343,513 | B1 | | 2/2002 | Yost et al. ..................... 73/645 |
| 2002/0009204 | A1 | * | 1/2002 | Matsumura .................. 381/98 |
| 2004/0064043 | A1 | * | 4/2004 | Rielly et al. ................. 600/437 |
| 2004/0077947 | A1 | * | 4/2004 | Migita ........................ 600/447 |

FOREIGN PATENT DOCUMENTS

WO    WO 98/46139    * 10/1998

OTHER PUBLICATIONS

J. H. Cantrell, W. T. Yost, S. Razvi, Peter Li; "Effective Nonlinearity Parameters of Aluminum Alloys as a Function of Volume Fraction of Second Phase Precipitates;" 1986 Ultrasonics Symposium Proceedings; IEEE; pp. 1075-1078.

John H. Cantrell; "Residual Strains from Lattice-Generated Stochastic Nonlinear Acoustic Radiation Fields in Solids;" 1986 Ultrasonics Symposium Proceedings; IEEE; pp. 1079-1082.

John A. Cantrell; "Cyrstalline Structure Dependence of Acoustic Nonlinearity Parameters;" 1987 Ultrasonics Symposium Proceedings; IEEE; pp. 425-428.

John A. Cantrell; "Nonlinear Phenomena in Solid State Physics and Technology;" 1990 Ultrasonics Symposium Proceedings; IEEE; pp. 1255-1261.

John H. Cantrell and William T. Yost; "Nonlinear Ultrasonic Characterization of Fatigue Microstructures;" International Journal of Fatigue; vol. 23; 2001; pp. 487 - 490.

Dimitri M. Donskoy and Alexander M. Sutin; "Vibro-Acoustic Modulation Nondestructive Evaluation Technique;" Journal of Intelligent Material Systems and Structures, vol. 9; Sep. 1998; pp. 765-771.

(Continued)

*Primary Examiner*—Hezron Williams
*Assistant Examiner*—Rose M. Miller
(74) *Attorney, Agent, or Firm*—Penny A. Clarke; Patrick K. Patnode

(57) ABSTRACT

A method for determining incipient mechanical failure of an object includes insonifying the object with ultrasonic energy at a selected fundamental frequency. Amplitude data is acquired from the insonified object at the fundamental frequency and at a second harmonic of the fundamental frequency, and a non-linear acoustic image is generated from the amplitude data at the fundamental frequency and the second harmonic frequency.

28 Claims, 3 Drawing Sheets

OTHER PUBLICATIONS

J. Frouin, J. Maurer, Sathish, D. Eylon, J. K. Na, T.E. Matikas; "Real-Time Monitoring of Acoustic Linear and Nonlinear Behavior of Titanium Alloys During Cyclic Loading;" Materials Research Society Symposium—Proceedings, vol. 591; 2000; pp. 79-84.

D. C. Hurley, W. T. Yost, E. S. Boltz, and C. M. Fortunko; "Experimental Comparison of Ultrasonic Techniques to Determine the Nonlinearity Parameter;" 1996 Ultrasonics Symposium Proceedings; IEEE; pp. 495-498.

Young-Chul Jung and Tribikram Kundu; "Ultrasonic Response to Material Fatigue;" Proceedings of the SPIE, vol. 4335; 2001; pp. 180-187.

Peter Li, John H. Cantrell Jr. and William T. Yost; "Thermal Strains and Acoustic Nonlinearity in Crystalline Solids;" 1984 Ultrasonics Symposium Proceedings; IEEE; pp. 955-957.

Peter Li, William T. Yost, John H. Cantrell, and Kamel Salama; "Dependence of Acoustic Nonlinearity Parameter of Second Phase Precipitates of Aluminum Alloys;" 1985 Ultrasonics Symposium Proceedings; IEEE; pp. 1113-1115.

Peter B. Nagy; "Fatigue Damage Assessment by Nonlinear Ultrasonic Materials Characterization;" Ultrasonics, vol. 36; Feb. 1998; pp. 375-381.

W.P Winfree, P. Li, and J. H. Cantrell Jr.; "Harmonic Generation of Short Ultrasonic Pulses;" 1982 Ultrasonics Symposium Proceedings; IEEE; pp. 1026-1028.

H. Yang, W. T. Yost, and J. H. Cantrell; "Effect of Aging on the Third-Order Elastic Moduli of 18Ni Maraging Steel;" 1987 Ultrasonics Symposium Proceedings; IEEE; pp. 425-428.

EP Search Report, EP04256524, Feb. 15, 2005.

* cited by examiner

INSPECTION METHOD AND APPARATUS FOR DETERMINING INCIPIENT MECHANICAL FAILURE

BACKGROUND OF THE INVENTION

The present disclosure relates generally to ultrasonic, non-destructive testing methods and, more particularly, to an ultrasonic inspection method and system for determining incipient mechanical failure.

Many mechanical failure modes include a long-duration first step in which microstructural damage and/or change accumulates in a region, followed thereafter by occurrence of observable cracks and failure. Of the overall service lifetime of a part, only a small amount of life remains once cracks are observable.

Cracks that are above certain threshold sizes, and within certain specified regions, may be detected by existing ultrasound or eddy current techniques. For example, in conventional ultrasound harmonic imaging, ultrasound signals or pulses are transmitted at fundamental frequencies, and echo signals are received by a transducer. Discontinuities, such as cracks, can be detected when their echoes are greater than that of the background noise.

Unfortunately, by the time a crack can be detected through such methodologies, the part has essentially failed. For example, fatigue cracks in titanium objects become detectable when only about 10% of life is remaining. The presence of an identified crack signifies the part has exhausted its life. Additionally, the presence of cracks in a particular part may prevent that part from being repaired and returned to service. Thus, it would be desirable to be able to detect incipient damage while the part is still repairable.

There are at least two noteworthy applications in which incipient mechanical failure analysis can be applied. The first relates to detection of incipient dwell-time fatigue in titanium alloy aircraft engine compressor forgings, and the second relates to detection of creep damage in structural applications such as aircraft engine and land gas turbine airfoils and disks. Dwell-time fatigue arises from the anisotropy of modulus and limited slip systems in titanium. Thus, if cyclic stresses (near the yield stress) are applied with hold times to a titanium body, then grains elastically deform to different degrees due to their individual crystallographic orientation with respect to the applied stress. In addition, some grains may begin plastic yielding while others do not. This process applied cyclically can lead to buildup of high stresses at grain (or colony) boundaries. An unfavorably oriented grain or colony of grains can crack by cleavage, wherein such a cleavage crack will lead to premature failure of the part. However, dwell-time fatigue cannot be detected by current techniques until there is a crack present.

BRIEF DESCRIPTION OF THE INVENTION

The above discussed and other drawbacks and deficiencies of the prior art are overcome or alleviated by a method for determining incipient mechanical failure of an object. In an exemplary embodiment, the method includes insonifying the object with ultrasonic energy at a selected fundamental frequency. Amplitude data is acquired from the insonified object at the fundamental frequency and at the second harmonic of the fundamental frequency, and a non-linear acoustic image is generated from the amplitude data at the fundamental frequency and the second harmonic frequency.

In another aspect, a method for determining incipient mechanical failure of an object includes insonifying the object with ultrasonic energy at a selected fundamental frequency using at least one of a backscatter scan and a surface wave scan. A broadband transducer is focused so as to detect amplitude data from the insonified object at the fundamental frequency and the second harmonic of said fundamental frequency. The amplitude data at the fundamental frequency and the second harmonic of the fundamental frequency are digitized and stored, and a non-linear acoustic image is generated from the amplitude data at the fundamental frequency and the second harmonic frequency.

In still another aspect, a system for determining incipient mechanical failure of an object includes a broadband transducer for insonifying the object with ultrasonic energy at a selected fundamental frequency through at least one of a backscatter scan and a surface wave scan. The broadband transducer is focused so as to detect amplitude data from the insonified object at the fundamental frequency and a second harmonic of said fundamental frequency. A pulser receiver receives detected signals from the transducer, and a data acquisition computer stores the amplitude data at the fundamental frequency and a second harmonic of the fundamental frequency in a digitized format. The stored amplitude data at the fundamental frequency and the second harmonic frequency is used to generate a non-linear acoustic image.

BRIEF DESCRIPTION OF THE DRAWINGS

Referring to the exemplary drawings wherein like elements are numbered alike in the several Figures.

DETAILED DESCRIPTION OF THE INVENTION

Disclosed herein is a method for non-destructive detection of those regions of an object in which mechanical failure is incipient (i.e., prior to actual nucleation of a micro-defect). Briefly stated, the method includes insonifying a subject part at an input frequency or frequencies, and noting those regions of the part in which there is a higher-than-background generation of harmonics of the input frequencies. This information may be generated and displayed by scanning a part in a manner similar to a C-scan, but distinguished from a conventional C-scan procedure by displaying the intensity of the ratio of the harmonics to the input frequencies and/or the spatial derivative of that intensity, rather than just the overall intensity of all sound reflected or transmitted.

Figure 1:
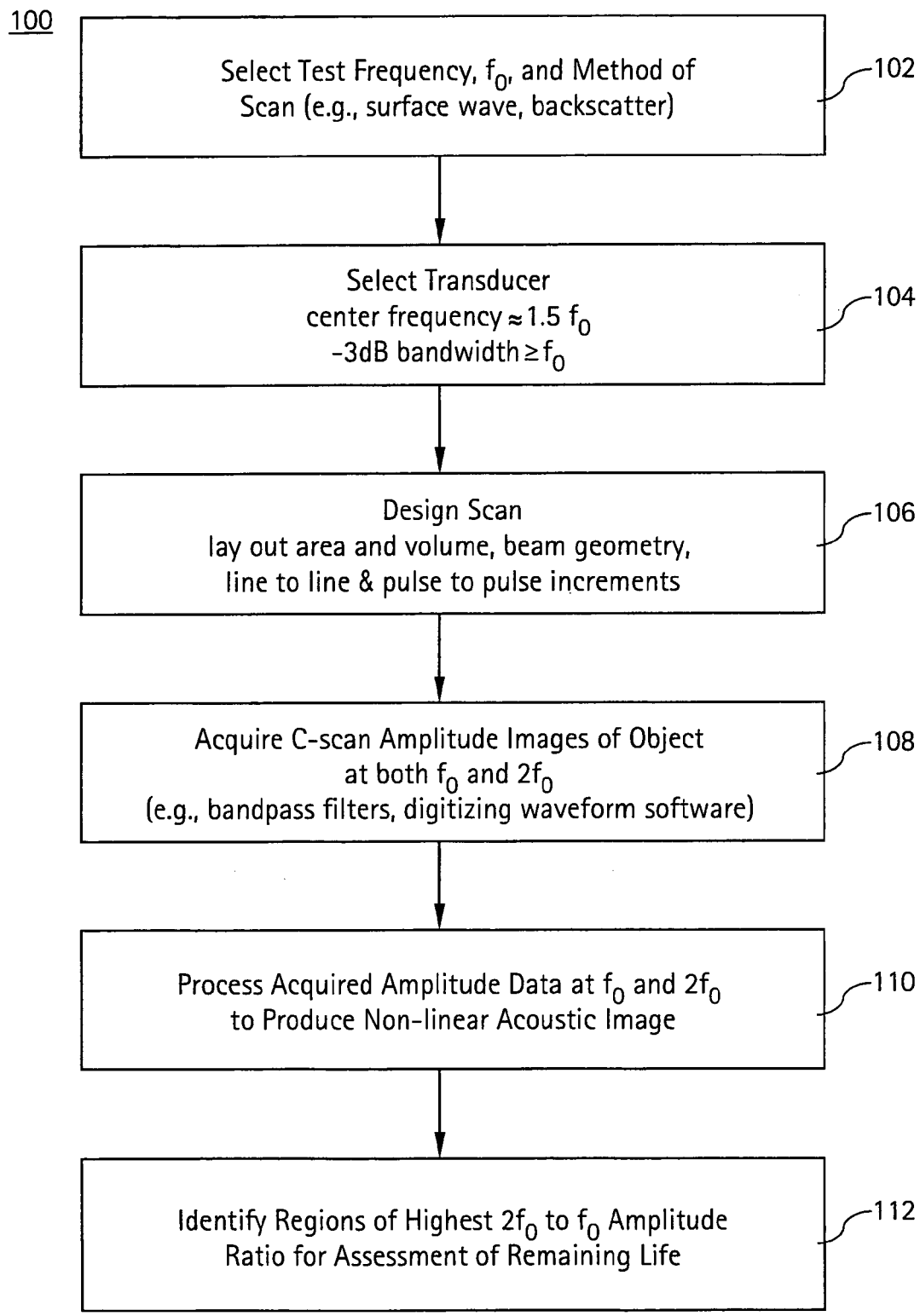
FIG. 1 is a block diagram illustrating a method for determining incipient mechanical failure of an object, in accordance with an embodiment of the invention.

Referring initially to FIG. 1, there is shown a block diagram illustrating a method 100 for determining incipient mechanical failure of an object, in accordance with an embodiment of the invention. The method 100 begins at block 102, in which a test frequency, $f_0$, is selected, as well as the particular type of scan (e.g., surface wave, backscatter). The type of scan will, in turn, be determined based on the location of the area of interest with respect to the surface of the object. Then, at block 104, a suitable transducer is selected such that both the fundamental test frequency, $f_0$, and the second harmonic of the fundamental frequency, $2f_0$, are detectable. For example, a broadband transducer having at least a −3 dB bandwidth of $f_0$, and a center frequency of about $1.5f_0$ should be able to transmit a focused beam at $f_0$, and receive backscattered signals at both $f_0$ and $2f_0$.

The transducer may include a pair of confocal elements focused by the same curvature to a common focal zone. A thinner of the two confocal elements may be used to receive the signals at $2f_0$, and as a matching layer for the transmitting element. By using confocal elements, the transmitting element can receive the fundamental frequency in pulse-echo, and the receiving element can receive the second harmonic.

In one embodiment, the input insonifying excitation is implemented via a pulse radio frequency (RF) driver, using a number (N) of wavelengths of the fundamental frequency as the input burst. The pulse length should be selected long enough so that the second harmonic component of the pulse power spectrum is sufficiently attenuated (e.g., by about 20 dB or more with respect to the amplitude of the fundamental frequency). On the other hand, the pulse length should also be selected short enough so that the material region, producing the echoes containing both fundamental and second harmonic components, is resolvable from the entry-surface echoes by the transducer. An approximation of the power spectrum amplitude of the RF input insonification pulse is given by the expression:

$$\frac{\sin[(N\pi/f_0)(f_0 - f)]}{[(N\pi/f_0)(f_0 - f)]}$$

Accordingly, the above expression shows that a suitable number of wavelengths ($\lambda$) for the input pulse at the fundamental frequency is $10\lambda$.

Proceeding now to block 106 of FIG. 1, method 100 continues by designing the parameters of the scan itself, including for example, the layout area and volume of the object, the beam geometry, and the line-to-line and pulse-to-pulse increments. For a backscatter image, the transducer should be located at a position such that the focal length thereof corresponds to a depth in the object that is at least twice the length of the excitation pulse length. Thus, for example, using a $10\lambda$ input pulse, the area of interest should be at least $20\lambda$ below the surface of the object in order to isolate the desired first and second harmonic signals from the area of interest from reflected signals at the surface of the object. The −6 dB beam diameter at frequency $2f_0$ is approximately equal to $1.03\lambda$ F/d: wherein the wavelength $\lambda$ refers to the wavelength at $2f_0$, and is thus also expressed by $1.03(c/2f_0)(F/d)$; wherein c is the velocity of the acoustic signals in the material of the object; F is the focal length of the transducer lens; and d is the diameter of the transducer lens. Furthermore, the depth of focus of the transducer for a backscatter scan is approximately equal to $4\lambda (F/d)^2$, or $4(c/2f_0)(F/d)^2$.

The volume from which the second harmonic echoes are received by the transducer is defined by the second harmonic wavelength, and is substantially smaller than the region insonified by the input fundamental frequency. The difference in length of depth of focus can be accommodated by setting the signal-gate (the time region over which a signal is recorded from each pulse) to be that of the depth of focus of the second harmonic, or shorter; the difference in cross sectional area of focus can be accommodated by suitable amplification of the second harmonic signal, where the value of that amplification will be selected after consideration of the nature of the material microstructure and how that microstructure scatters sound.

For generating/detecting a surface wave image, the transducer is focused at a sufficient numerical aperture so as to include the surface wave (or Rayleigh wave) incident angle. The position of the transducer focal point is placed at a sufficient depth beneath the entry surface to resolve the surface wave from the direct reflection of the input excitation such that a gated surface wave pulse is isolated in time from the direct reflection pulse.

Regardless of the type of scan implemented, the resulting ultrasonic images of the object are acquired in a manner that captures amplitude data at both $f_0$ and $2f_0$, as illustrated in block 108 of FIG. 1. As is discussed in further detail hereinafter, the $f_0$ and $2f_0$ signals may be obtained in a number of ways. In one embodiment, separate bandpass filters are used to detect the $f_0$ and $2f_0$ signals before the signals are digitized and stored in a data acquisition computer. For each image taken, 8 bits (or more) per pixel may be used to represent the amplitude data at each of the two frequencies. Alternatively, the output of a pulser receiver in communication with the transducer may be coupled to a waveform-digitizer such that the entire gated waveform for each ultrasonic pulse is acquired and stored in a data acquisition file. In this embodiment, the digitization rate should be at $8f_0$ (or more) for the entire gated signal to be recorded. Thus, for $10\lambda$ pulses, about 80 bytes are needed for full waveform acquisition and processing in software.

Once the amplitude data at $f_0$ and $2f_0$ is acquired, it is processed in order to produce a non-linear acoustic image, as shown in block 110. Generally, this non-linear acoustic image is presented as ratio of the amplitude of the second harmonic signal and the square of the amplitude of the fundamental frequency signal. In one specific embodiment, a "beta" image is constructed in accordance with the expression:

$$\beta = (8/ak^2)(A_2/A_1^2) = (8c^2 A_2)/(4\pi^2 a f_o^2 A_1^2),$$

wherein $A_2$ is the amplitude of the second harmonic frequency ($2f_0$) component, $A_1$ is the amplitude of the fundamental frequency ($f_0$) component, $k=2\pi f_0/c$, c is the velocity of the acoustic signals in the material of the object, and a is a scanning parameter representing the focal depth (of a backscatter scan) or the entry circle (of a surface wave scan). In addition to generating a beta image, a spatial derivative image of the beta intensities may also be produced.

Finally, as shown in block 112, the processed amplitude data is used to identify regions of highest $2f_0$ to $f_0$ amplitude ratio for assessing remaining life of the object. The assessment may include, for example, a graphic display on a color or gray scale to highlight the regions of highest $2f_0$ to $f_0$ amplitude ratio, or may also include a presentation/analysis of the spatial derivative of the non-linear amplitude ratios of the second harmonic and fundamental frequencies.

Figure 2:
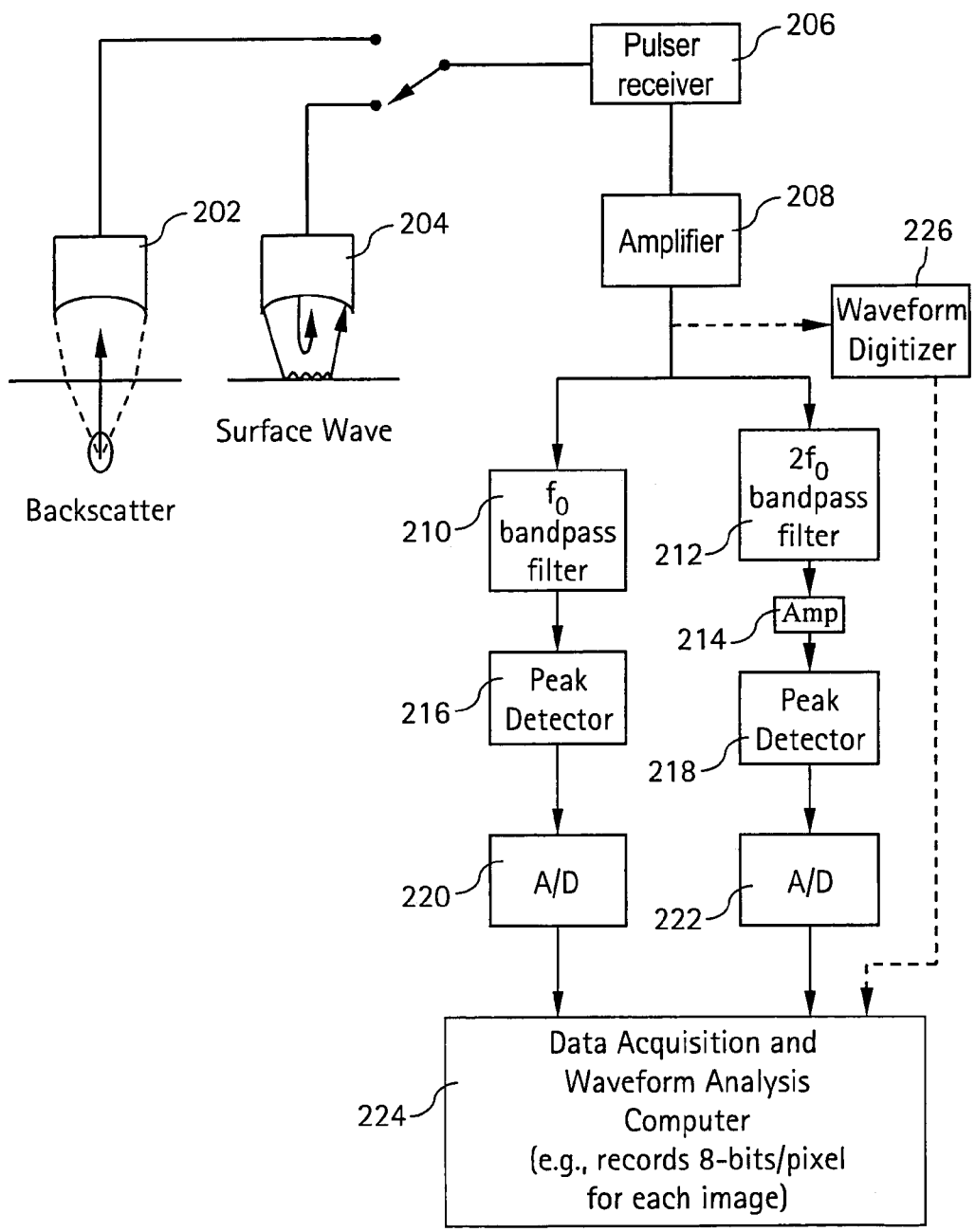
FIG. 2 is a schematic diagram illustrating an exemplary system that may be used to implement the incipient mechanical failure inspection method shown in FIG. 1, in accordance with a further aspect of the present invention.

FIG. 2 is a schematic diagram illustrating an exemplary system 200 that may be used to implement the incipient mechanical failure inspection method 100, in accordance with a further aspect of the present invention. The system 200 illustrates a first broadband transducer 202 configured for a backscatter scan and a second broadband transducer 204 configured for a surface wave scan. In either case, the return signals detected by transducer 202 or transducer 204 are received by a pulser receiver 206 and amplified by amplifier 208.

As stated previously, separation of the $f_0$ and $2f_0$ signals may be carried out through the use of a first bandpass filter 210 centered at $f_0$ and a second bandpass filter 212 centered at $2f_0$. An additional amplifier 214 may be used to amplify the signals passed through the $2f_0$ bandpass filter 212. A pair of peak detectors 216, 218 receive the filtered signals from $f_0$ bandpass filter 210 and $2f_0$ bandpass filter 212, respectively. Then, the $f_0$ and $2f_0$ signals are digitized by A/D converters 220, 222 and stored by data acquisition computer 224 for subsequent production of a non-linear acoustic image based on the $f_0$ and $2f_0$ amplitude data. As indicated by the dashed lines in FIG. 2, the amplified signals from the pulser receiver 206 may alternatively be inputted into a waveform digitizer 226 for Fourier analysis thereof, and the digitized amplitude data directly stored into the data acquisition computer 224.

Figure 3:
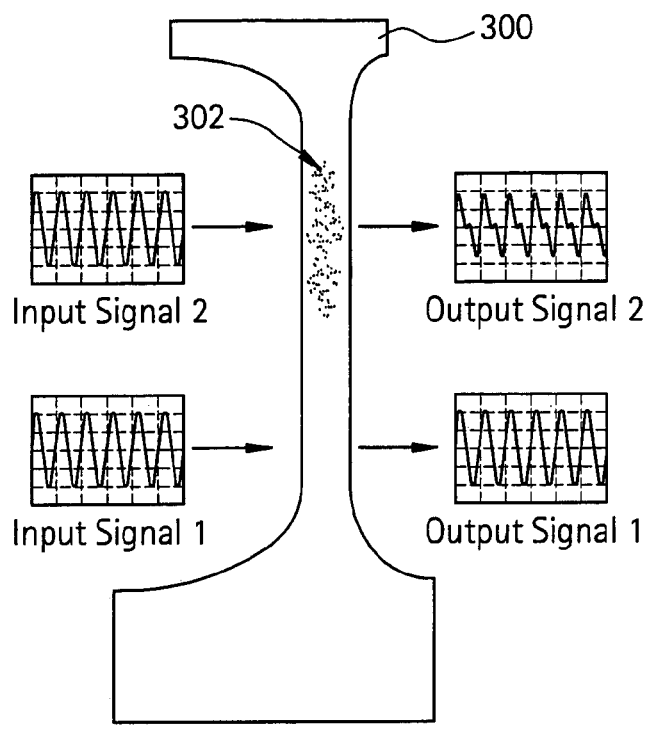
FIG. 3 schematically depicts an exemplary object having a region of latent mechanical damage therein.
Figure 4:
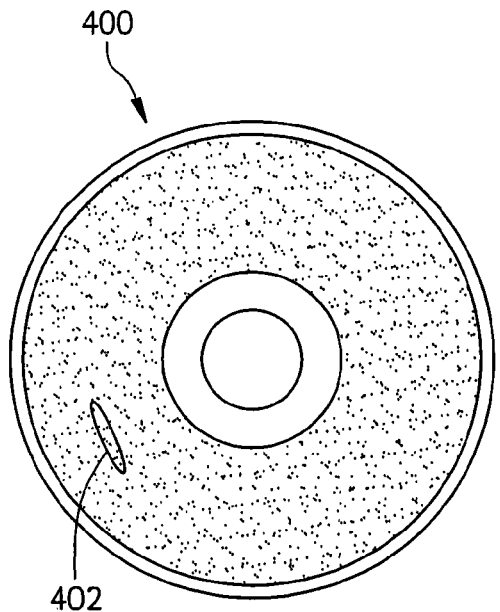
FIG. 4 illustrates an object disk that contains a region of mechanical damage.
Figure 5:
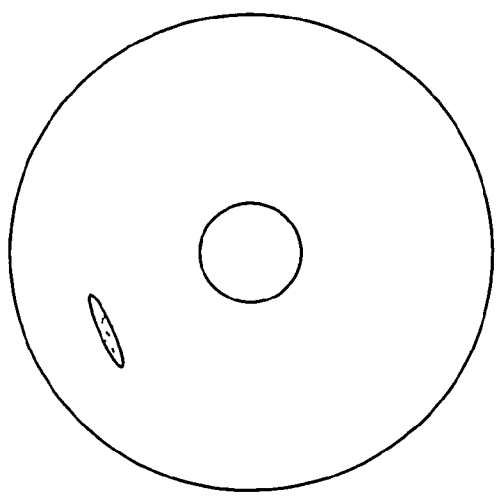
FIG. 5 is an exemplary $2f_0$ to $f_0$ amplitude ratio intensity plot corresponding to the object disk of FIG. 4.

FIG. 3 schematically depicts an exemplary object 300 having a region 302 of latent mechanical damage therein. As shown by a first set of input and output signals, when the input energy is focused on "undamaged" areas of the object 300, there is a negligible amount of second harmonic distortion on the output signal. On the other hand, when the input energy is focused on damaged region 302, the resulting output signal will have a significant second harmonic component associated therewith. Thus, when scanned, those locations in the object corresponding to a relatively high amplitude of second harmonic signals are candidates for incipient mechanical failure locations. In FIG. 4, there is shown an object disk 400 that contains a region 402 of mechanical damage. Through the scanning and non-linear image generation of $f_0$ and $2f_0$ amplitude data as discussed above, regions of highest $2f_0$ to $f_0$ amplitude ratio may be identified and displayed, such as shown in the exemplary amplitude intensity plot of FIG. 5.

As will be appreciated, the above described method and system embodiments should not be construed so as to limit the generation of the amplitude data in a specific manner. For example, it is contemplated that other combinations of $2f_0$ and $f_0$ amplitudes (linear or non-linear) may be used in the scanning method, so long as regions in which the calibrated intensity of a harmonic strongly deviates from background (or in which there is a strong spatial variability of harmonic intensity) are identified as regions of mechanical damage (e.g., incipient dwell-time fatigue damage). Accordingly, parts in which failure is incipient can be detected more reliably and earlier than through conventional techniques. This will permit more reliable operation of the part, as well as allow for longer inspection intervals for certain applications. Moreover, parts may be inspected to determine suitability for repair and return to service, in which a measure of assurance is provided that repaired parts will not fail by premature nucleation of cracks from incipient damage present (and heretofore undetectable).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining incipient mechanical failure of an object, the method comprising:
   insonifying the object with ultrasonic energy at a selected fundamental frequency;
   acquiring amplitude data from the insonified object at said fundamental frequency and a second harmonic of said fundamental frequency; and
   generating a non-linear acoustic image from said amplitude data at said fundamental frequency and said second harmonic frequency,
   wherein said acquiring amplitude data is implemented with a broadband transducer having a center frequency at about 1.5 times said fundamental frequency.

2. The method of claim 1, wherein said non-linear acoustic image is generated by using a ratio of said amplitude data at said second harmonic frequency and the square of said amplitude data at said fundamental frequency.

3. The method of claim 2, wherein said non-linear acoustic image is a beta image constructed in accordance with the expression:

$$\beta = (8/ak^2)(A_2/A_1^2) = (8c^2A_2)/(4\pi^2 a f_o^2 A_1^2),$$

wherein $A_2$ is the amplitude of said second harmonic frequency ($2f_0$), $A_1$ is the amplitude of the fundamental frequency ($f_0$), $k = 2\pi f_0/c$, wherein c is the velocity of the acoustic signals in the material of the object, and a is a scanning parameter.

4. The method of claim 1, wherein said transducer is also used for said insonifying the object with ultrasonic energy.

5. The method of claim 1, further comprising implementing at least one of a backscatter scan and a surface wave scan.

6. The method of claim 5, wherein said insonifying the object with ultrasonic energy is implemented with an excitation pulse having a pulse length of at least $10\lambda$, wherein $\lambda$ is the wavelength of the excitation pulse at said fundamental frequency.

7. The method of claim 6, wherein for a backscatter scan, said transducer is focused to a depth within the object of at least about $20\lambda$ with respect to an outer surface of the object.

8. The method of claim 5, wherein for a surface scan, said transducer is focused so as to include the Rayleigh wave critical angle of the insonified material.

9. The method of claim 8, wherein for a surface scan, said transducer is also focused so as to isolate a surface wave from a direct reflection wave.

10. A method for determining incipient mechanical failure of an object, the method comprising:
    insonifying the object with ultrasonic energy at a selected fundamental frequency using at least one of a backscatter scan and a surface wave scan;
    focusing a broadband transducer so as to detect amplitude data from the insonified object at said fundamental frequency and a second harmonic of said fundamental frequency;
    digitizing and storing said amplitude data at said fundamental frequency and a second harmonic of said fundamental frequency; and
    generating a non-linear acoustic image from said amplitude data at said fundamental frequency and said second harmonic frequency,
    wherein said broadband transducer has a center frequency of about 1.5 times said fundamental frequency.

11. The method of claim 10, wherein said non-linear acoustic image is determined by using a ratio of said amplitude data at said second harmonic frequency and the square of said amplitude data at said fundamental frequency.

12. The method of claim 11, wherein said non-linear acoustic image is a beta image constructed in accordance with the expression:

$$\beta = (8/ak^2)(A_2/A_1^2) = (8c^2A_2)/(4\pi^2 a f_o^2 A_1^2),$$

wherein $A_2$ is the amplitude of said second harmonic frequency ($2f_0$), $A_1$ is the amplitude of the fundamental frequency ($f_0$), $k=2\pi f_0/c$, wherein c is the velocity of the acoustic signals in the material of the object, and a is a scanning parameter.

13. The method of claim 10, wherein said transducer is also used for said insonifying the object with ultrasonic energy.

14. The method of claim 10, wherein for a surface scan, said transducer is focused so as to include the Rayleigh wave critical angle of the insonified material.

15. The method of claim 14, wherein for a surface scan, said transducer is also focused so as to isolate a surface wave from a direct reflection wave.

16. The method of claim 10, wherein said digitizing and storing said amplitude data at said fundamental frequency and a second harmonic of said fundamental frequency is implemented using a first bandpass filter centered at said fundamental frequency and a second bandpass filter centered at said second harmonic of said fundamental frequency.

17. The method of claim 10, wherein said digitizing and storing said amplitude data at said fundamental frequency and a second harmonic of said fundamental frequency is implemented using waveform-analysis software.

18. A method for determining incipient mechanical failure of an object, the method comprising:

insonifying the object with ultrasonic energy at a selected fundamental frequency using at least one of a backscatter scan and a surface wave scan;

focusing a broadband transducer so as to detect amplitude data from the insonified object at said fundamental frequency and a second harmonic of said fundamental frequency;

digitizing and storing said amplitude data at said fundamental frequency and a second harmonic of said fundamental frequency; and generating a non-linear acoustic image from said amplitude data at said fundamental frequency and said second harmonic frequency, wherein said insonifying the object with ultrasonic energy is implemented with an excitation pulse having a pulse length of at least $10\lambda$, wherein $\lambda$ is the wavelength of the excitation pulse at said fundamental frequency.

19. The method of claim 18, wherein for a backscatter scan, said transducer is focused to a depth within the object of at least about $20\lambda$ with respect to an outer surface of the object.

20. A system for determining incipient mechanical failure of an object, comprising:

a broadband transducer for insonifying the object with ultrasonic energy at a selected fundamental frequency through at least one of a backscatter scan and a surface wave scan;

said broadband transducer focused so as to detect amplitude data from the insonified object at said fundamental frequency and a second harmonic of said fundamental frequency;

a pulser receiver for receiving detected signals from said transducer; and a data acquisition computer for storing said amplitude data at said fundamental frequency and a second harmonic of said fundamental frequency in a digitized format, wherein said stored amplitude data at said fundamental frequency and said second harmonic frequency is used to generate a non-linear acoustic image, and wherein said broadband transducer has a center frequency of about 1.5 times said fundamental frequency.

21. The system of claim 20, wherein said non-linear acoustic image is determined by using a ratio of said amplitude data at said second harmonic frequency and the square of said amplitude data at said fundamental frequency.

22. The system of claim 21, wherein said non-linear acoustic image is a beta image constructed in accordance with the expression:

$$\beta = (8/ak^2)(A_2/A_1^2) = (8c^2 A_2)/(4\pi^2 a f_o^2 A_1^2),$$

wherein $A_2$ is the amplitude of said second harmonic frequency ($2f_0$), $A_1$ is the amplitude of the fundamental frequency ($f_0$), $k=2\pi_0/c$, wherein c is the velocity of the acoustic signals in the material of the object, and a is a scanning parameter.

23. The system of claim 20, wherein for a surface scan, said transducer is focused so as to include the Rayleigh wave critical angle of the insonified material.

24. The system of claim 23, wherein for a surface scan, said transducer is also focused so as to isolate a surface wave from a direct reflection wave.

25. The system of claim 20, further comprising:

a first bandpass filter for receiving detected signals from said pulser receiver, said first bandpass filter centered at said fundamental frequency; and a second bandpass filter for receiving detected signals from said pulser receiver, said second bandpass filter centered at said second harmonic of said fundamental frequency;

wherein outputs of said first and said second bandpass filter are converted to said digitized format for storage in said data acquisition computer.

26. The system of claim 20, further comprising waveform-analysis software for receiving detected signals from said pulser receiver said waveform-analysis software further outputting digitized amplitude data at said fundamental frequency and said second harmonic of said fundamental frequency for storage in said data acquisition computer.

27. A system for determining incipient mechanical failure of an object, comprising:

a broadband transducer for insonifying the object with ultrasonic energy at a selected fundamental frequency through at least one of a backscatter scan and a surface wave scan;

said broadband transducer focused so as to detect amplitude data from the insonified object at said fundamental frequency and a second harmonic of said fundamental frequency;

a pulser receiver for receiving detected signals from said transducer; and a data acquisition computer for storing said amplitude data at said fundamental frequency and a second harmonic of said fundamental frequency in a digitized format, wherein said stored amplitude data at said fundamental frequency and said second harmonic frequency is used to generate a non-linear acoustic image, and wherein said transducer emits an excitation pulse having a pulse length of at least $10\lambda$, wherein $\lambda$ is the wavelength of said excitation pulse at said fundamental frequency.

28. The system of claim 27, wherein for a backscatter scan, said transducer is focused to a depth within the object of at least about $20\lambda$ with respect to an outer surface of the object.

* * * * *